US011529123B2

(12) United States Patent
Labyed

(10) Patent No.: US 11,529,123 B2
(45) Date of Patent: Dec. 20, 2022

(54) RELATIVE BACKSCATTER COEFFICIENT IN MEDICAL DIAGNOSTIC ULTRASOUND

(71) Applicant: Siemens Medical Solutions USA, Inc., Malvern, PA (US)

(72) Inventor: Yassin Labyed, Maple Valley, WA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 979 days.

(21) Appl. No.: 15/077,751

(22) Filed: Mar. 22, 2016

(65) Prior Publication Data

US 2017/0273667 A1    Sep. 28, 2017

(51) Int. Cl.
  *A61B 8/00*    (2006.01)
  *A61B 8/08*    (2006.01)
  *G01S 7/52*    (2006.01)
  *A61B 8/14*    (2006.01)

(52) U.S. Cl.
  CPC ............ *A61B 8/5223* (2013.01); *A61B 8/469* (2013.01); *G01S 7/52036* (2013.01); *A61B 8/14* (2013.01); *A61B 8/4494* (2013.01); *A61B 8/56* (2013.01)

(58) Field of Classification Search
  CPC ......... A61B 8/14; A61B 8/4494; A61B 8/461; A61B 8/48; A61B 8/56; A61B 8/5223; G01S 7/52085
  See application file for complete search history.

(56) References Cited

U.S. PATENT DOCUMENTS

| 5,097,836 | A | * | 3/1992 | Yamada | A61B 8/08 600/443 |
| 6,110,118 | A | * | 8/2000 | Guracar | A61B 8/08 600/453 |
| 8,192,362 | B2 | * | 6/2012 | Kolios | A61B 8/08 600/437 |
| 2005/0053305 | A1 | * | 3/2005 | Li | A61B 8/00 382/260 |
| 2012/0259225 | A1 | * | 10/2012 | Tashiro | A61B 8/14 600/443 |
| 2014/0163369 | A1 | * | 6/2014 | Nair | A61B 5/4869 600/437 |
| 2016/0327524 | A1 | * | 11/2016 | Wang | G01N 29/46 |

OTHER PUBLICATIONS

Fereshteh Aalamifar, Hassan Rivaz, Juan J. Cerrolaza, James Jago, Nabile Safdar, Emad M. Boctor, Marius George Linguraru, "Classification of kidney and liver tissue using ultrasound backscatter data," (Mar. 17, 2015), Proc. SPIE, 9419.*
Yassin Labyed, Timothy A. Bigelow,"A theoretical comparison of attenuation measurement techniques from backscattered ultrasound echoes," (2011), J. Acoustical Society of America, 2316.*

(Continued)

*Primary Examiner* — Keith M Raymond
*Assistant Examiner* — Milton Truong

(57) ABSTRACT

In backscatter coefficient imaging, a backscatter coefficient of one region of interest relative another region of interest is used to avoid calibration. The system effects are removed by using a frequency-dependent measure of the backscatter. The relative frequency-dependent backscatter coefficient is determined by an ultrasound scanner.

14 Claims, 3 Drawing Sheets

(56) References Cited

OTHER PUBLICATIONS

Michael L. Oelze, Jonathan Mamou, "Review of quantitative ultrasound: envelope statistics and backscatter coefficient imaging and contributions to diagnostic ultrasound," (Feb. 2016), IEEE Trans Ultrason Ferroelectr Freq Control, 336.*

Jenderka, K. V. et al. "Tissue characterization by imaging the local frequency dependent relative backscatter coefficient". Proc. SPIE 3982, Medical Imaging 2000: Ultrasonic Imaging and Signal Processing, p. 270-277 (Year: 2000).*

S. Dasarathy et al. "Validity of real time ultrasound in the diagnosis of hepatic steatosis: A prospective study". Journal of Hepatology 51 (2009) 1061-1067 (Year: 2009).*

S. C. Lin et al. "Noninvasive Diagnosis of Nonalcoholic Fatty Liver Disease and Quantification of Liver Fat Using a New Quantitative Ultrasound Technique". Clin Gastroenterol Hepatol. Jul. 2015 ; 13(7): 1337-1345 (Year: 2015).*

Wilson, Thaddeus Andrew. "In vivo frequency-dependent backscatter estimations in liver". The University of Wisconsin—Madison. ProQuest Dissertations Publishing, 2000. 9981932. (Year: 2000).*

Insana, Michael F., and Timothy J. Hall. "Parametric ultrasound imaging from backscatter coefficient measurements: Image formation and interpretation." Ultrasonic Imaging 12.4 (1990): 245-267.

Von Volkmann, Hilde Løland, et al. "Quantitative measurement of ultrasound attenuation and hepato-renal index in non-alcoholic fatty liver disease." Medical ultrasonography 15.1 (2013): 16.

Yao, Lin Xin, James A. Zagzebski, and Ernest L. Madsen. "Backscatter coefficient measurements using a reference phantom to extract depth-dependent instrumentation factors." Ultrasonic Imaging 12.1 (1990): 58-70.

Zelber-Sagi, Shira, et al. "Comparison of fatty liver index with noninvasive methods for steatosis detection and quantification." World J Gastroenterol 19.1 (2013): 57-64.

* cited by examiner

RELATIVE BACKSCATTER COEFFICIENT IN MEDICAL DIAGNOSTIC ULTRASOUND

BACKGROUND

This present embodiments relate to medical diagnostic ultrasound. In particular, ultrasound is used to provide backscatter information.

Conventional B-mode imaging provides qualitative information about the scattering properties of tissues. Several factors affect the brightness of different tissues, including gain, focusing, log compression, transducer response, beamforming settings, and/or other system settings of the ultrasound scanner. These factors make it difficult to obtain quantitative values of the tissue backscatter.

The absolute backscatter may be estimated. The backscatter measure is calibrated using a reference phantom or a planar reflector to remove the system or other effects. These calibration-based approaches are subject to errors because the attenuation along the propagation path to a region of interest in a given patient is unknown and because of differences in speed of sound between the tissue sample and the reference phantom. Calibration is also time consuming and difficult.

A relative backscatter may be used. The Hepato-renal index (HRI) is the ratio between the median B-mode brightness level of the liver and right kidney cortex. Using the ratio of brightness values does not accurately remove system-specific effects, so the HRI may lack a desired level of accuracy or precision.

BRIEF SUMMARY

By way of introduction, the preferred embodiments described below include a method, system, computer readable medium, and instructions for backscatter coefficient imaging. A backscatter coefficient of one region of interest relative another region of interest is used to avoid the calibration. The system effects are removed by using a frequency-dependent measure of the backscatter. The relative frequency-dependent backscatter coefficient is determined by an ultrasound scanner.

In a first aspect, a method is provided for backscatter coefficient imaging with a medical diagnostic ultrasound scanner. First and second regions of interest are identified in a scan region of a patient. Ultrasound data representing acoustic echoes from the first and second regions are received from the medical diagnostic ultrasound scanner. A transform processor of the medical diagnostic ultrasound scanner calculates first and second spectra for the first and second regions, respectively, from the ultrasound data. The transform processor determines a relationship of the first spectrum with the second spectrum. A value that is a function of the relationship is displayed on a display.

In a second aspect, a non-transitory computer readable storage medium has stored therein data representing instructions executable by a programmed processor for backscatter coefficient ultrasound imaging. The storage medium includes instructions for measuring acoustic backscatter from different areas of a patient, transforming the acoustic backscatter from the different areas into frequency-dependent backscatter, determining a relative backscatter coefficient from the frequency-dependent backscatter between the different areas, and transmitting the relative backscatter coefficient.

In a third aspect, a system is provided for estimating frequency-dependent relative backscatter coefficient. A receive beamformer is configured to output samples for different regions of a patient. A transform estimator is configured to transform the samples into frequency-dependent backscatter for the different regions and to calculate a ratio of the frequency-dependent backscatter of the different regions as the frequency-dependent relative backscatter coefficient. A display is configured to display information, which is a function of the frequency-dependent relative backscatter coefficient.

The present invention is defined by the following claims, and nothing in this section should be taken as a limitation on those claims. Further aspects and advantages of the invention are discussed below in conjunction with the preferred embodiments.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Based on spectral analysis of radio frequency (RF) echo signals or other backscatter information from ultrasound, system specific effects are corrected. The relative frequency-dependent backscatter coefficient is measured from the spectra.

Unlike estimating the absolute backscatter coefficient, the proposed approach does not require the use of a reference phantom or reference plate, and does not suffer from as many errors caused by differences in sound speed and attenuation between the tissue sample and the reference phantom. Other approaches estimate the relative backscatter based on the grayscale values of the B-mode images. These approaches do not use spectral information and suffer from errors because the system effects are not removed effectively.

One application that may benefit from the proposed relative frequency-dependent backscatter coefficient measure is staging fatty liver disease. Fatty liver is hyperechoic compared to the kidney. The relative backscatter coefficient or parameters derived from the relative backscatter coefficient may potentially be used to stage fatty liver disease. Other applications may also benefit from the relative backscatter coefficient.

Figure 1:
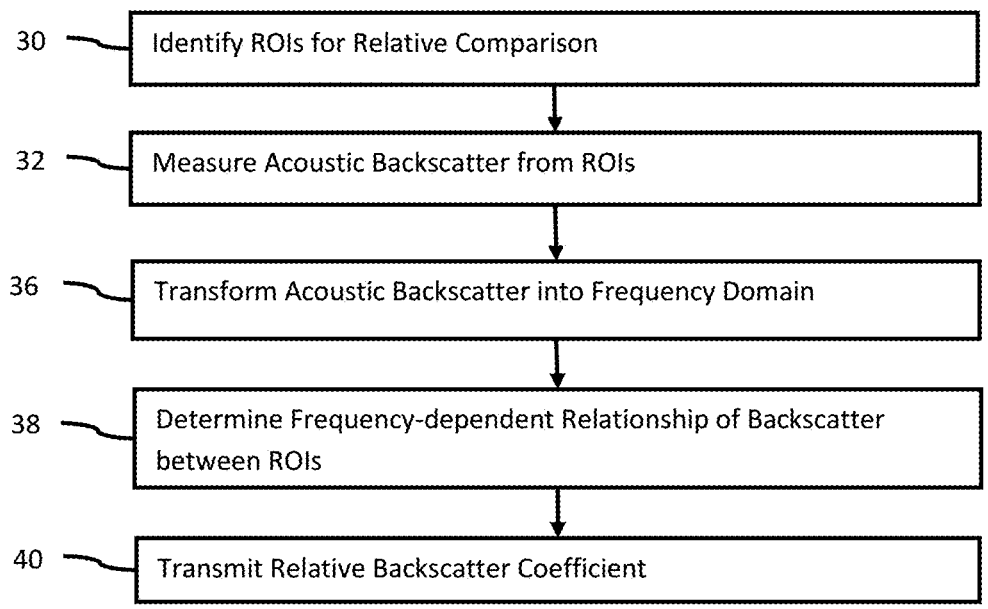
FIG. 1 is a flow chart of one embodiment of a method for backscatter coefficient imaging with a medical diagnostic ultrasound scanner.

FIG. 1 shows one embodiment of a flow chart diagram of a method for backscatter coefficient imaging with a medical diagnostic ultrasound scanner. Backscatter, such as from beamformed samples, is measured in different regions of interest. The backscatter for each region is converted to the frequency domain so that a relative frequency-dependent backscatter coefficient may be calculated.

Figure 5:
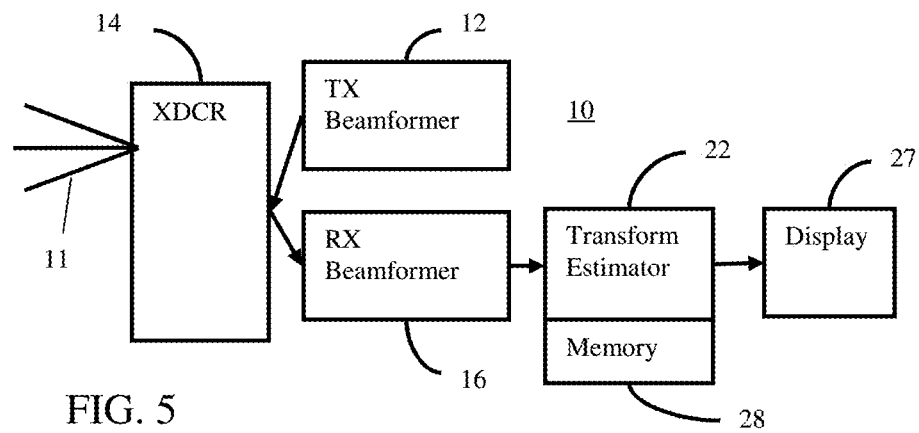
FIG. 5 is a block diagram of one embodiment of a system for backscatter coefficient imaging with a medical diagnostic ultrasound.

The method is performed by the ultrasound imaging system 10 of FIG. 5, the transform estimator 22, or a different system and/or processor. For example, the ultrasound imaging system 10 acquires backscatter from multiple regions, transforms the backscatter into the frequency domain, and calculates a relative backscatter coefficient from the spectra of the regions. The receive beamformer 16 acquires the backscatter and the transform estimator 22 calculates the relative backscatter coefficient from the acquired backscatter.

The acts of FIG. 1 are performed in the order shown (top to bottom) or a different order. For example, the acoustic backscatter is measured for a field of view in act 32 prior to identifying the regions in the field of view in act 30.

Additional, different, or fewer acts than shown in FIG. 1 may be used. For example, act 32 is not performed. As another example, acts for scanning and generating B-mode or other ultrasound images for identifying the regions or interest are added.

In act 30, two or more regions of interest are identified. The ultrasound scanner scans the patient. Any field of view may be scanned, such as a field of view representing both the liver and kidney. Any scan mode may be used, such as a B-mode scan.

The user designates the regions of interest. The results of the scan are displayed as an image. The user designates the locations of the regions of interest in the image. Any designation may be used, such as using a user interface to place a rectangular box, square box, circle, or other area shape. Where the scan is of a three-dimensional region or volume, the user may indicate a location and size for a cuboid, prism, ovoid, or other three-dimensional shape designating a region of interest. Alternatively, the user traces the regions of interest. Any now known or later developed user input designating a region of interest may be used.

In alternative embodiments, a segmentor or processor identifies the regions of interest. Using thresholding, classification, detection, or other image process, locations representing a contiguous region of interest are identified. The regions of interest are segmented or otherwise located from the data representing the scan field of the ultrasound scanner. Semi-automatic, such as the user selecting locations and the processor determining the shape and/or size of the regions about the locations, may be used.

The regions of interest are at the same depth. The center of each region is at a same depth. Alternatively or additionally, the deepest and shallowest depths are the same. In one embodiment, the size and shape as well as the depths of the different regions are the same or substantially the same. Substantially accounts for sub-pixel or sampling resolution, so provides for a depth within one pixel or cycle of the sample frequency. The regions may be symmetrically located a same distance away on opposite sides of the center scan line (i.e., on opposite sides of the center scan line for the field of view). Alternatively, the regions are at different depths, sizes, and/or non-symmetrical lateral positions.

Figure 2:
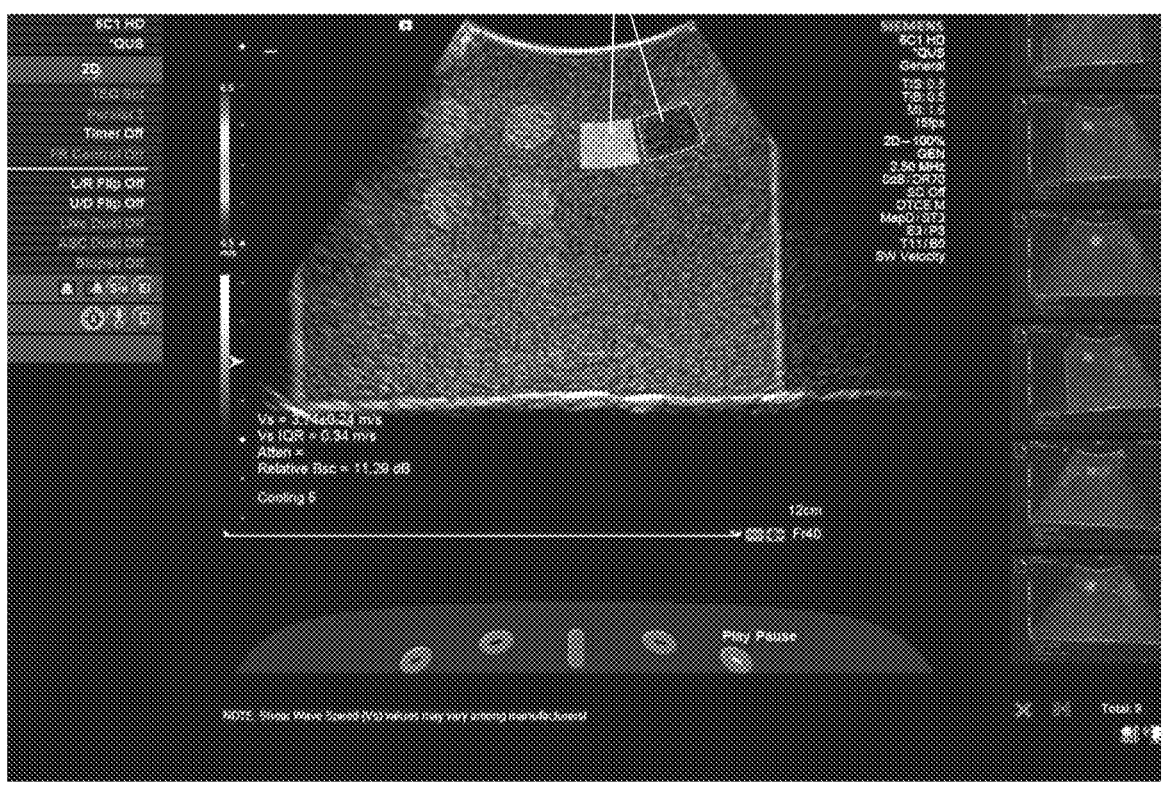
FIG. 2 is an example image with two regions of interest at a same depth.

FIG. 2 shows an image with two regions of interest 46. The image is a shear velocity image, but B-mode, flow mode, or other images may be used. The user places two boxes or region of interest designators. The regions of interest 46 are the same size and shape and are at a same depth, but are not at symmetrical locations relative to each other about the center scan line. Other regions 46 may be used with greater or lesser separation between the regions 46.

One region 46 is positioned in a background or reference location (e.g., the kidney), and the other region 46 is positioned for an organ or tissue of interest (e.g., the liver). The regions are for part or all of an organ. The kidney is used as a reference for backscatter. The liver is being examined to diagnosis fatty liver disease. An amount of deviation of the backscatter from the liver from the reference kidney may be indicative of fatty liver disease.

In act 32, the ultrasound scanner measures the acoustic backscatter from the regions of interest of the patient. The measurement occurs as a subsequent scan after the identification of the regions of interest. The entire scan field or just the regions of interest are scanned. Alternatively, the measurement occurs as part of a scan that previously occurred, such as scanning, generating an image, using the image to identify the regions, and using the data from or used to create the image as the measure.

The acoustic backscatter is measured for each one, two, or three-dimensional region. The same or different sampling distance (e.g., depth spacing between samples and/or scan line spacing) is used for measuring the different regions. Samples representing the different sampling locations in each region at a given period are acquired.

The measured backscatter is radio frequency (RF) or in-phase and quadrature (IQ) data output by a receive beamformer. In response to a transmission of acoustic energy (e.g., a transmit beam), acoustic echoes impinge upon elements of a transducer. The elements convert the acoustic echoes into electrical signals. The receive beamformer coherently sums the signals from different elements to determine the response of tissue at particular sample locations. The output of the receive beamformer is RF or IQ data. In alternative embodiments, backscatter is measured from data at other parts of the ultrasound imaging pipeline, such as element signals prior to beamforming, B-mode data after detection, or image data after mapping to display values.

In act 36, the measured acoustic backscatter is transformed into the frequency domain. The ultrasound scanner or a transform processor applies a Fourier or other transform to the acoustic backscatter, creating frequency-dependent backscatter.

The transform results in a spectrum for each region of interest. The backscatter samples (i.e., ultrasound data) from a given region are transformed, providing a spectrum for that region. By Fourier transforming the ultrasound data for one region, a spectrum for that one region is created. By Fourier transforming the ultrasound data for another region, a spectrum for that other region is created.

Where the region includes samples along more than one scan line, the samples of each scan line may be separately transformed. The frequency response as a function of depth or subject to the same beamforming is transformed. As a result, multiple spectra (i.e., line spectra or spectrum for each scan line) are provided for a given region. The spectra for the different scan lines in a same region are averaged, providing a spectrum for the region of interest. Other combinations may be used, such as (a) performing one transform using the samples from all the sample locations in the region or interest (e.g., 2D Fourier transform) or (b) transforming across lateral locations and averaging the resulting spectra from the different depths.

In act 38, the ultrasound scanner, transform processor, controller, or other device determines a relationship between the spectra of the different regions of interest. Where there are two regions, the relationship of the spectrum of one region with the spectrum of the other region is determined.

Relationships between three or more regions may be determined as different sets of relationships or a single relationship between the three or more regions. The relationship is a relative backscatter coefficient. Relative is used to denote that the relationship is between two or more different things—regions in this example. Coefficient is used to denote that a value or parameter represents a measure of the relationship. Backscatter denotes that the coefficient is based on at least some backscatter information.

The relationship is determined from the frequency-dependent backscatter. The relationship is between the backscatter of different regions at one frequency, over a range of frequencies, or using any of the spectral information. The relationship is of a relative frequency-dependent backscatter coefficient.

In one embodiment, the relationship is a ratio. The ratio of the spectrum from one region to the spectrum from another region is calculated. In one embodiment, the ratio is determined in log space, such as calculating the log of the spectra and subtracting one from the other. Other relationships using values of the spectra from different regions may be used.

The ratio of the frequency-dependent backscatter may remove the transducer response, gain, focusing effects, attenuation, and/or other effects of the settings of the ultrasound scanner. The power spectrum (PS) function is given by:

$$PS(f) = G(f)D(f)BSC(f)e^{-4\alpha f z} \quad (1)$$

where G is the combined transducer effects for transmitting and receiving, D represents the beamforming and diffraction effects, BSC is the backscatter coefficient, a is attenuation, z is depth, and f is frequency. The power spread function is used for quantitative ultrasound and may be used for the relative frequency-dependent backscatter coefficient.

By using relative information from the two different regions, G and D may be dropped from the equation. The ratio of power spectra from two regions of interest (ROIs) is given by:

$$\frac{PS_{Roi1}(f)}{PS_{Roi2}(f)} = \frac{G_{Roi1}(f)D_{Roi1}(f)BSC_{Roi1}(f)}{G_{Roi2}(f)D_{Roi2}(f)BSC_{Roi2}(f)} e^{-4(\alpha_{Roi1}-\alpha_{Roi2})fz} \quad (2)$$

Roi1 and Roi2 are at the same depth, therefore it may be assumed that:

$$G_{Roi1}(f)D_{Roi1}(f)e^{-4(\alpha_{Roi1})fz} \approx G_{Roi2}(f)D_{Roi2}(f)e^{-4(\alpha_{Roi2})fz} \quad (3)$$

The system effects and attenuation along the propagation path are eliminated, resulting in equation 1 becoming:

$$\frac{PS_{Roi1}(f)}{PS_{Roi2}(f)} \approx \frac{BSC_{Roi1}(f)}{BSC_{Roi2}(f)}, \quad (4)$$

providing the relative backscatter coefficient as the ratio of frequency-dependent backscatter. Other approaches resulting in cancelation of D and/or G may be used.

Figure 3:
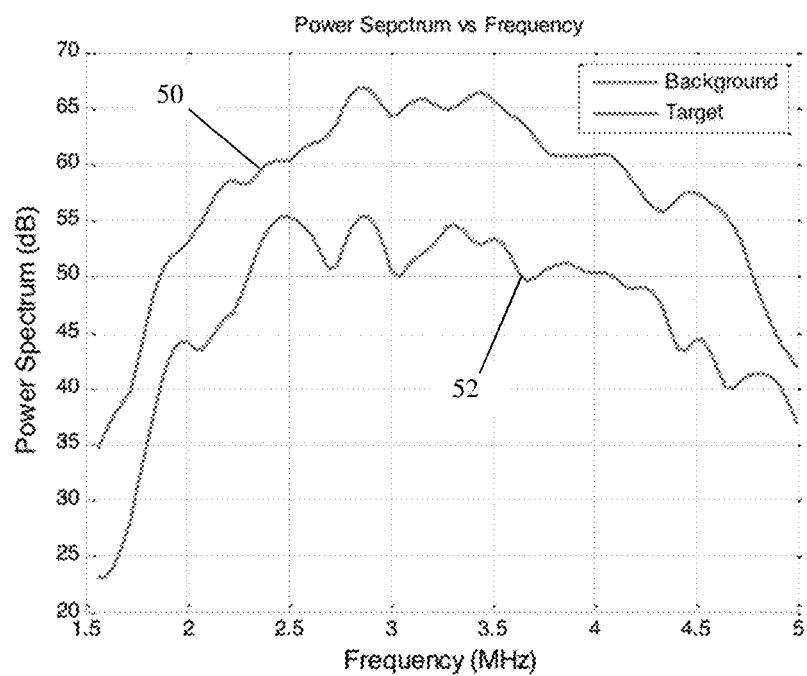
FIG. 3 shows example spectra for the two regions of interest of FIG. 2.
Figure 4:
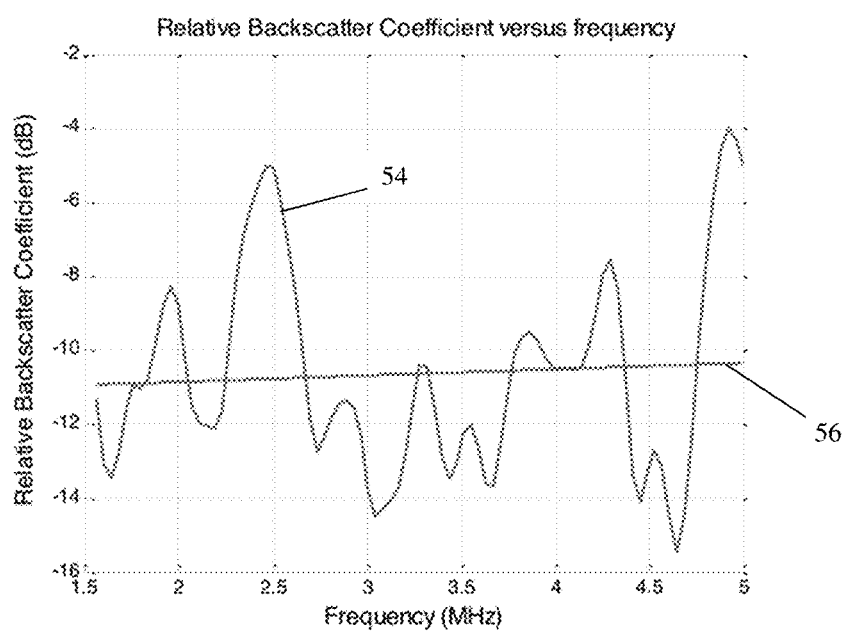
FIG. 4 shows an example graph of relationships of the two spectra of FIG. 3.

FIG. 3 shows the spectra 50, 52 for the two regions of interest 46 of FIG. 2. The reference spectrum 52 has lower power than the spectrum 50 of the tissue of interest. At any given frequency or over a range of frequencies, the ratio is calculated. FIG. 4 shows the ratio 54 (i.e., relative backscatter coefficient) as a function of frequency for the spectra 50, 52 of FIG. 3. In this example, the relative backscatter coefficient 54 between the two ROIs is 11.29 dB at 3 MHz.

Other expressions of the relationship may be used. FIG. 4 shows a line 56 linearly fit to the ratio as a function of frequency. The slope or intercept of the line 56 indicate a measure of the relative backscatter coefficient over a range (e.g., 1.5 to 5 MHz) of frequencies. Different ranges and/or expressions may be used.

Referring again to FIG. 1, the relative backscatter coefficient is transmitted in act 40. The transmission is from a processor, such as the transform processor, within the ultrasound scanner, and/or from the ultrasound scanner. The transmission is to another device, such as a memory, display, network, server, workstation, patient record database, and/or picture archiving and communications server. The relationship is transmitted as data or imbedded in an image.

In one embodiment, the transmission is to a display. A value that is a function of the relative backscatter coefficient is displayed. The value is displayed as alphanumeric text. The value is the relationship itself (e.g., ratio at a given frequency or average ratio over a range of frequencies) and/or is derived from the relationship (e.g., intercept and/or slope of a fit line). In alternative or additional embodiments, the value is included as part of a graph, such as displaying the ratio over frequency and/or fit line of FIG. 4.

The value is displayed in decibels. Alternatively, the value is displayed or normalized to a percentage or quantity between 0 and 1. For the normalization, any values may be used for the maximum and minimum, such as values determined experimentally to represent the expected distribution. Other units of measure of the value may be used.

The value is displayed alone or with another image. For example, the B-mode image, an image of spectra (e.g., FIG. 3), or other image is provided with the value representing the relationship.

FIG. 5 shows one embodiment of a medical system 10 for estimating the frequency-dependent relative backscatter coefficient. The medical system 10 is an ultrasound scanner using relative backscatter and frequency dependence to avoid or limit calibration and/or reduce the effects of system settings on backscatter calculation. The medical system 10 implements the method of FIG. 1 or another method.

The medical system 10 includes a transmit beamformer 12, a transducer 14, a receive beamformer 16, a transform estimator 22, a memory 28, and a display 27. Additional, different or fewer components may be provided. For example, the medical system 10 includes a B-mode or other detector. As another example, the transform estimator 22, memory 28, and/or display 27 are provided without the front-end components, such as the transmit and receive beamformers 12, 16. In yet another example, a user interface including a user input (e.g., mouse, trackball, keyboard, buttons, knobs, sliders, and/or touch pad) is provided for user indication of the regions of interest on an image.

In one embodiment, the medical system 10 is a medical diagnostic ultrasound system. In an alternative embodiment, the system 10 is a computer or workstation.

The transducer 14 is an array of a plurality of elements. The elements are piezoelectric or capacitive membrane elements. The array is configured as a one-dimensional array, a two-dimensional array, a 1.5 D array, a 1.25 D array, a 1.75 D array, an annular array, a multidimensional array, a wobbler array, combinations thereof, or any other now known or later developed array. The transducer elements transduce between acoustic and electric energies. The transducer 14 connects with the transmit beamformer 12 and the receive beamformer 16 through a transmit/receive switch, but separate connections may be used in other embodiments.

The transmit and receive beamformers 12, 16 are a beamformer for scanning with the transducer 14. The transmit beamformer 12, using the transducer 14, transmits one or more beams to scan a region. Vector®, sector, linear or other scan formats may be used. The receive lines and/or transmit beams are distributed in the scan region. The receive beamformer 16 samples the receive beams at different depths.

The transmit beamformer 12 is a processor, delay, filter, waveform generator, memory, phase rotator, digital-to-analog converter, amplifier, combinations thereof or any other now known or later developed transmit beamformer components. In one embodiment, the transmit beamformer 12 digitally generates envelope samples. Using filtering, delays, phase rotation, digital-to-analog conversion and amplification, the desired transmit waveform is generated. Other waveform generators may be used, such as switching pulsers or waveform memories.

The transmit beamformer 12 is configured as a plurality of channels for generating electrical signals of a transmit waveform for each element of a transmit aperture on the transducer 14. The waveforms are unipolar, bipolar, stepped, sinusoidal, or other waveforms of a desired center frequency or frequency band with one, multiple or fractional number of cycles. The waveforms have relative delay and/or phasing and amplitude for focusing the acoustic energy. The transmit beamformer 12 includes a controller for altering an aperture (e.g. the number of active elements), an apodization profile (e.g., type or center of mass) across the plurality of channels, a delay profile across the plurality of channels, a phase profile across the plurality of channels, center frequency, frequency band, waveform shape, number of cycles, and/or combinations thereof. A transmit beam origin, orientation, and focus are generated based on these beamforming parameters.

The receive beamformer 16 is a preamplifier, filter, phase rotator, delay, summer, base band filter, processor, buffers, memory, combinations thereof or other now known or later developed receive beamformer components. The receive beamformer 16 is configured into a plurality of channels for receiving electrical signals representing echoes or acoustic energy impinging on the transducer 14. A channel from each of the elements of the receive aperture within the transducer 14 connects to an amplifier and/or delay. An analog-to-digital converter digitizes the amplified echo signal. The digital radio frequency received data is demodulated to a base band frequency. Any receive delays, such as dynamic receive delays and/or phase rotations, are then applied by the amplifier and/or delay. A digital or analog summer combines data from different channels of the receive aperture to form one or a plurality of receive beams. The summer is a single summer or cascaded summer. In one embodiment, the beamform summer is configured to sum in-phase and quadrature channel data in a complex manner such that phase information is maintained for the formed beam. In alternative embodiments, the receive beamformer sums radio frequency data. Other receive beamformers may be used.

The receive beamformer 16 is configured to form receive beams in response to the transmit beams. For example, the receive beamformer 16 receives one, two, or more receive beams in response to each transmit beam. The phase rotators, delays, and/or summers may be repeated for parallel receive beamformation. One or more of the parallel receive beamformers may share parts of channels, such as sharing initial amplification. The receive beams are collinear, parallel and offset or nonparallel with the corresponding transmit beams.

The receive beamformer 16 is configured to output samples for different regions of a patient. The receive beamformer 16 outputs spatial samples representing different spatial locations of a scanned region. Once the channel data is beamformed or otherwise combined to represent spatial locations along the scan lines 11, the data is converted from the channel domain to the image data domain. By scanning with transmit and receive beamformation in any pattern (e.g., sector, Vector, or linear), a field of view is scanned. The regions of interest are within the field of view, so samples of the regions are output. Alternatively, the scanning is controlled to just scan the regions of interest. The locations sampled by receive beamforming are located in the regions of interest.

The transform estimator 22 is a digital signal processor, a general processor, an application specific integrated circuit (ASIC), field programmable gate array (FPGA), control processor, digital circuitry, analog circuitry, graphics processing unit, combinations thereof, or other now known or later developed device for transforming data to the frequency domain and/or calculating the relative frequency-dependent backscatter coefficient. The transform estimator 22 is configured by hardware, firmware, and/or software, such as operating pursuant to instruction provided in the memory 28 or a different memory. In one embodiment, the transform estimator 22 is a digital signal processor, ASIC, or FPGA specifically for applying a Fourier transform, and another device (e.g., calculator or processor) calculates the coefficient from an output of the transform device. In other embodiments, the transform estimator 22 is a programmable device that performs both the transform and calculation.

The transform estimator 22 is configured to transform the samples into frequency-dependent backscatter for the different regions. The IQ, RF, or other samples output by the receive beamformer 16 are transformed using a Fourier or other transform into the frequency domain. Other measures of backscatter may be transformed in other embodiments, such as transforming B-mode detected data or image data.

The data for each region of interest is transformed separately, creating different or separate spectra. In one embodiment, the spectrum for a given region is an average or other combination of spectra from different sub-sets of data for the region. For example, the samples from each line over the range of depths within the region are transformed. The resulting spectra from the different scan lines or receive beams are combined, providing the spectrum for the region. Other combinations or transformations may be used.

The transform estimator 22 is configured to calculate a ratio of the spectra of the different regions as the relative frequency-dependent backscatter coefficient. Other relationships than a ratio may be calculated. The frequency-dependent relationship of backscatter between different regions is determined by the transform estimator 22, a controller, image processor, or other device.

The samples or ultrasound data may be used to generate an image. A B-mode detector, flow estimator (e.g., Doppler processor), or other detector may be provided for detecting characteristics from the receive beamformed samples. A B-mode detector detects the intensity or power of the acoustic backscatter. A flow estimator detects the velocity, energy, or variance of moving objects (e.g., tissue or fluid). The detection may be used to generate an image from which regions of interest are selected. Alternatively, other scanning is performed to generate the image, and the samples used for calculating the relative backscatter coefficient are from a separate scan.

An image processor and/or the transform estimator 22 are configured to generate an image. The image includes the relative backscatter coefficient. For example, a graph of the coefficient as a function of frequency (see ratio 54 of FIG. 4) and/or a fit line (see line 56 of FIG. 4) is generated as an image. As another example, alphanumeric text is generated as an image, such as 11.29 dB at 3 MHz or a table of different differences as a function of frequency. In other embodiments, the backscatter coefficient is provided as an annotation on an image of the patient, such as on a B-mode image.

The memory 28 is video random access memory, random access memory, removable media (e.g. diskette or compact disc), hard drive, database, or other memory device for storing samples, spectra, backscatter coefficient, and/or images. The memory 28 is used by the transform estimator 22 for transforming samples to frequency space, calculating the backscatter coefficient, or other acts described for FIG. 1.

The instructions for implementing the processes, methods and/or techniques discussed above are provided on computer-readable storage media or memories, such as a cache, buffer, RAM, removable media, hard drive or other computer readable storage media, such as represented by the memory 28. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

The display 27 is a CRT, LCD, plasma, projector, monitor, printer, touch screen, or other now known or later developed display device. The display 27 receives RGB, other color values, or other values and outputs an image. The image may be a gray scale or color image. The image displays information that is a function of the frequency-dependent relative backscatter coefficient. A slope, intercept, ratio at one or more frequencies, or other indication of the relationship between backscatter spectra from different regions is displayed. Alphanumeric, graphical, annotation, or other representation of the coefficient or values derived from the coefficient is displayed in an image on the display 27. The image may or may not additionally represent the region of the patient scanned by the beamformer 12, 16 and transducer 14.

In one embodiment, an image representing at least one of the regions of interest is annotated or color coded to indicate a level of the coefficient relative to a disease reference. For example, different ranges of the relative frequency-dependent backscatter coefficient represent different stages of a disease (e.g., fatty liver disease). The image of or region of interest for the liver is color coded with a colors, shade, or brightness representing a given stages. Different colors, shades, and/or brightnesses represent different disease stages. The stage for that patient is indicated by color or other modulation of the region pixels. Textual indication may be used.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

I claim:

1. A method for backscatter coefficient imaging with a medical diagnostic ultrasound scanner, the method comprising:
    identifying first and second regions of interest in a scan region of a patient, the first region positioned in a kidney and the second region positioned in a liver;
    receiving, from the medical diagnostic ultrasound scanner, ultrasound data representing acoustic echoes from the first and second regions, the ultrasound data comprising in-phase and quadrature data output from a receive beamformer of the medical diagnostic ultrasound scanner;
    calculating, by a transform processor of the medical diagnostic ultrasound scanner, first and second spectra for the first and second regions, respectively, from the ultrasound data as the in-phase and quadrature data;
    determining, by the transform processor, a relationship of the first spectrum with the second spectrum; and
    displaying, on a display, an indication of fatty liver disease as a slope of a line fit to the relationship over frequency or an intercept of the line fit to the relationship over frequency of the first spectrum relative to the second spectrum from the in-phase and quadrature or radio frequency data.

2. The method of claim 1 wherein identifying comprises identifying the first and second regions with user input of two or three-dimensional designations of the first and second regions on a B-mode image generated by the medical diagnostic ultrasound scanner.

3. The method of claim 1 wherein calculating comprises Fourier transforming the ultrasound data for the first region and Fourier transforming the ultrasound data for the second region.

4. The method of claim 1 wherein calculating the first spectrum comprises calculating line spectra along each scan line in the first region of interest and averaging the line spectra, the first spectrum comprising the average of the line spectra.

5. The method of claim 1 wherein determining the relationship comprises determining a ratio of the first spectrum to the second spectrum.

6. The method of claim 1 wherein determining the relationship comprises subtracting a logarithm of the first spectrum from a logarithm of the second spectrum.

7. The method of claim 1 wherein determining the relationship comprises determining a relative frequency-dependent backscatter coefficient as the relationship.

8. The method of claim 1 wherein displaying comprises displaying a value of the slope or intercept in decibels or as a percentage or quantity normalized between 0 and 1.

9. A non-transitory computer readable storage medium having stored therein data representing instructions executable by a programmed processor for backscatter coefficient ultrasound imaging, the storage medium comprising instructions for:
- measuring acoustic backscatter from different areas of a patient, the different areas comprising kidney and liver areas;
- transforming the acoustic backscatter from the different areas into frequency-dependent backscatter;
- determining a relative backscatter coefficient at one frequency from the frequency-dependent backscatter between the different areas;
- determining a value indicative of fatty liver disease from the relative backscatter coefficient; and
- displaying a slope or an intercept over frequency range of a line fit to the frequency dependent backscatter from the different areas.

10. The non-transitory computer readable storage medium of claim 9 wherein measuring comprises receive beamforming from two or three-dimensional regions of interest.

11. The non-transitory computer readable storage medium of claim 9 wherein transforming comprises Fourier transforming.

12. The non-transitory computer readable storage medium of claim 9 wherein determining the relative backscatter coefficient comprises calculating a ratio of the frequency-dependent backscatter from the different areas.

13. A system for estimating frequency-dependent relative backscatter coefficient, the system comprising:
- a receive beamformer configured to output samples for different regions of a patient, the different regions being a liver region and a kidney region, the samples being in-phase and quadrature signals;
- a transform estimator configured to transform the in-phase and quadrature signals into frequency-dependent backscatter for the different regions, to calculate a ratio of the frequency-dependent backscatter of the different regions as the frequency-dependent relative backscatter coefficient, and to determine a slope or intercept over frequency range of a line fit to the frequency-dependent relative backscatter, the slope or intercept indicative of fatty liver disease; and
- a display configured to display an image showing the slope or intercept.

14. The system of claim 13 wherein the transform estimator is configured to transform the in-phase and quadrature signals into spectra as the frequency-dependent backscatter.

* * * * *